United States Patent
Levy et al.

(10) Patent No.: US 10,815,306 B2
(45) Date of Patent: Oct. 27, 2020

(54) HUMANIZED AND CHIMERIC MONOCLONAL ANTIBODIES TO CD81

(71) Applicant: The Board of Trustees of the Leland Stanford Junior University, Stanford, CA (US)

(72) Inventors: Shoshana Levy, Stanford, CA (US); Aurelien Marabelle, Sceaux (FR); Ranjani Rajapaksa, Mountain View, CA (US); Felipe Vences-Catalan, Stanford, CA (US); Chiung-Chi Kuo, Stanford, CA (US); Jie Liu, Palo Alto, CA (US); Ronald Levy, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/308,113

(22) PCT Filed: Jun. 14, 2017

(86) PCT No.: PCT/US2017/037533
§ 371 (c)(1),
(2) Date: Dec. 7, 2018

(87) PCT Pub. No.: WO2017/218691
PCT Pub. Date: Dec. 21, 2017

(65) Prior Publication Data
US 2019/0177425 A1    Jun. 13, 2019

Related U.S. Application Data

(60) Provisional application No. 62/351,054, filed on Jun. 16, 2016.

(51) Int. Cl.
| | | |
|---|---|---|
| *A61K 39/395* | (2006.01) | |
| *C07K 16/28* | (2006.01) | |
| *C07K 16/30* | (2006.01) | |
| *A61P 35/04* | (2006.01) | |
| *A61P 35/00* | (2006.01) | |
| *A61K 39/00* | (2006.01) | |

(52) U.S. Cl.
CPC .......... *C07K 16/2896* (2013.01); *A61P 35/00* (2018.01); *A61P 35/04* (2018.01); *A61K 2039/505* (2013.01); *C07K 2317/24* (2013.01); *C07K 2317/41* (2013.01); *C07K 2317/52* (2013.01); *C07K 2317/565* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 2008/0131912 A1 | 6/2008 | Tu et al. |
| 2009/0028851 A1 | 1/2009 | Stuhmer et al. |
| 2009/0053225 A1 | 2/2009 | Marzari et al. |
| 2012/0164160 A1 | 6/2012 | Sahin et al. |
| 2014/0030771 A1 | 1/2014 | Yu et al. |
| 2015/0139990 A1 | 5/2015 | Watanabe et al. |

FOREIGN PATENT DOCUMENTS

WO    2011016238    2/2011

OTHER PUBLICATIONS

MacCallunn et al. (1996). J. Mol. Biol. 262:732-745.*
De Pascalis et al. (2002). Journal of Immunology. 169:3076-3084.*
Casset et al. (2003). Biochemical and Biophysical Reseaerch Commmunications. 307:198-205.*
Chen et al. (1999). J. Mol. biol. 293:865-881.*
Wu et al. (1999). J. Mol. Biol. 294:151-162.*
Zimmerman et al., "Crystal Structure of a Full-Length Human Tetraspanin Reveals a Cholesterol-Binding Pocket", Nov. 3, 2016, Cell, pp. 1041-1051.e11, vol. 167, Issue 4, Elsevier, New York City, NY.
Xu et al., "Diversity in the CDR3 Region of VH Is Sufficient for Most Antibody Specificities", Immunity, Jul. 1, 2000, pp. 37-45, vol. 13, Issue 1, Elsevier, New York City, NY.
GenPept_S43103, Ig kappa chain V-J region (461 Vl)—mouse (fragment). GenPept Accession No. S43103, May 24, 2001, Retrieved from the Internet: <URL: https://www.ncbi.nlm.nih.gov/protein/S43103> Definition, Region, and Origin, the region between amino acid residues 56-62.
Sagi et al., "Complementary costimulation of human T-cell subpopulations by cluster of differentiation 28 (CD28) and CD81", Proc Natl Acad Sci USA, Jan. 31, 2012, pp. 1613-1618, 109 (5), National Academy of Sciences, Washington, D.C.
Vences-Catalan et al. (2019) "CD81 is a novel immunotherapeutic target for B cell lymphoma" J. Exp. Med, vol. 216 pp. 1497-1508.

* cited by examiner

*Primary Examiner* — Christine J Saoud
*Assistant Examiner* — Jon M Lockard
(74) *Attorney, Agent, or Firm* — Pamela J. Sherwood; Bozicevic, Field & Francis LLP

(57) ABSTRACT

Humanized or chimeric anti-CD81 (cluster of differentiation 81) monoclonal antibodies are provided. The antibodies bind to human CD81, and find use in various therapeutic methods, including without limitation the reduction or prevention of tumor metastasis. Further provided are heavy chain and light chain variable region sequences as well as associated complementarity-determining region (CDR) sequences.

11 Claims, 9 Drawing Sheets
Specification includes a Sequence Listing.

Amino acid sequences of VH genes:

```
                                        CDR1
SEQ ID NO:1    QIQLVQSGPELKKPGETVKISCKASGYIFTDDSIHWVKQAPGKG
SEQ ID NO:2    QVQLVQSGSELKKPGASVKVSCKASGYTFTDDSIHWVRQAPGQG
SEQ ID NO:3    QIQLVQSGSELKKPGASVKVSCKASGYIFTDDSIHWVKQAPGQG

CDR2
SEQ ID NO:1    LKWMGWINTETGEPTYADDFKGRFAFSLETSASTAYLQINNL
SEQ ID NO:2    LEWMGWINTETGEPTYADDFKGRFVFSLDTSVSTAYLQISSL
SEQ ID NO:3    LKWMGWINTETGEPTYADDFKGRFAFSLDTSVSTAYLQISSL

CDR3
SEQ ID NO:1    KNEDAATYFCARLSPVVVIFIYWGQGTLVTVSA
SEQ ID NO:2    KAEDTAVYYCARLSPVVVIFIYWGQGTLVTVSS
SEQ ID NO:3    KAEDTAVYYCARLSPVVVIFIYWGQGTLVTVSS
```

Amino acid sequences of VL genes:

```
                                        CDR1
SEQ ID NO:4    DIVMSQSPSSLAVSVGEKVTMSCKSSQSLLHSRTRKNYLAWFQ
SEQ ID NO:5    DIVMTQSPLSLPVTPGEPASISCKSSQSLLHSRTRKNYLAWYL
SEQ ID NO:6    DIVMTQSPLSLPVTPGEPASMSCKSSQSLLHSRTRKNYLAWFQ

CDR2
SEQ ID NO:4    QKPGQSPKLLIYWASTRESGVPDRFTGSGSGTDFTLTISSVQAE
SEQ ID NO:5    QKPGQSPQLLIYWASTRESGVPDRFSGSGSGTDFTLKISRVEAE
SEQ ID NO:6    QKPGQSPKLLIYWASTRESGVPDRFSGSGSGTDFTLKISRVEAE

CDR3
SEQ ID NO:4    DLAVYYCKQSYNLYAFGGGTKLEMR
SEQ ID NO:5    DVGVYYCKQSYNLYAFGQGTKLEIK
SEQ ID NO:6    DLAVYYCKQSYNLYAFGQGTKLEIK
```

FIG. 1

FIG. 4A
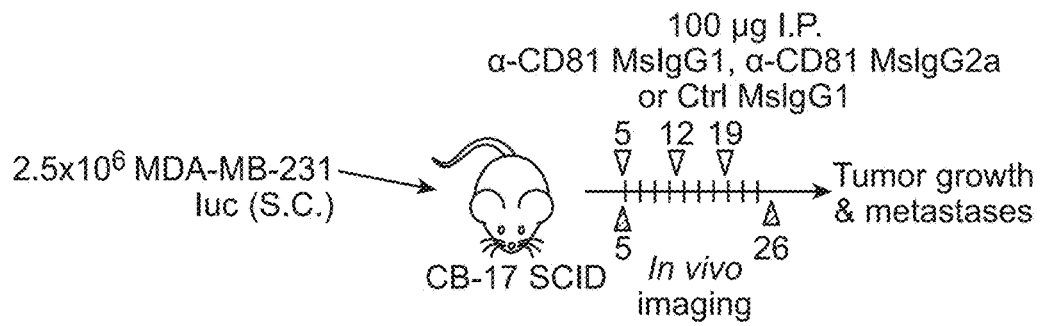
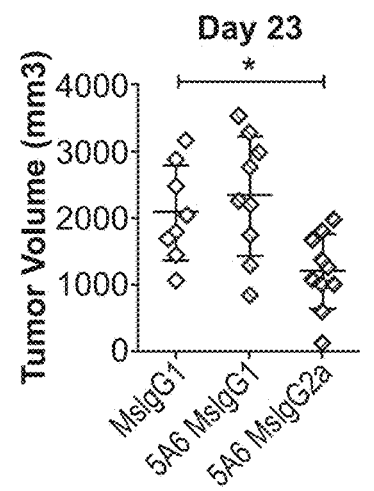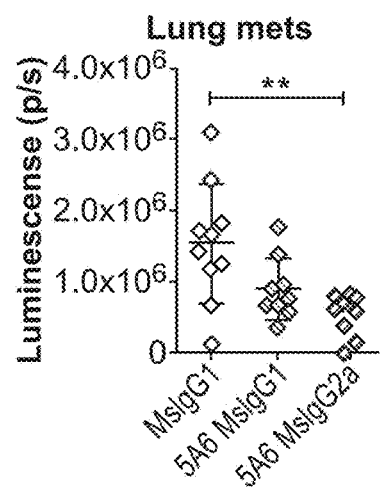
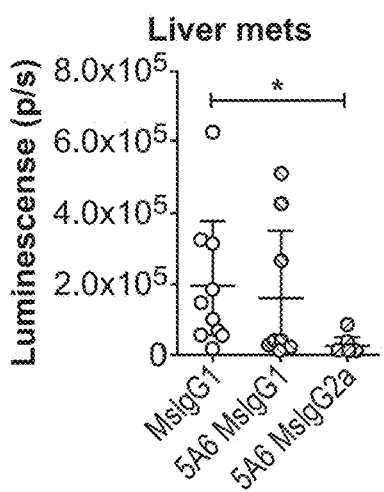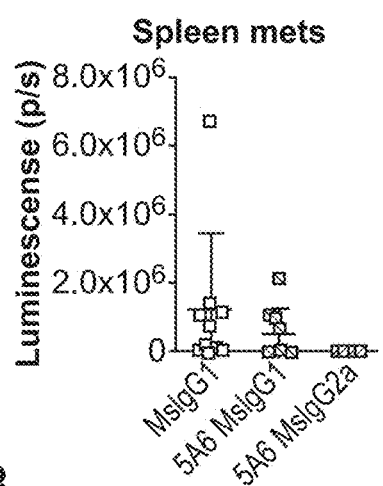
FIG. 4B

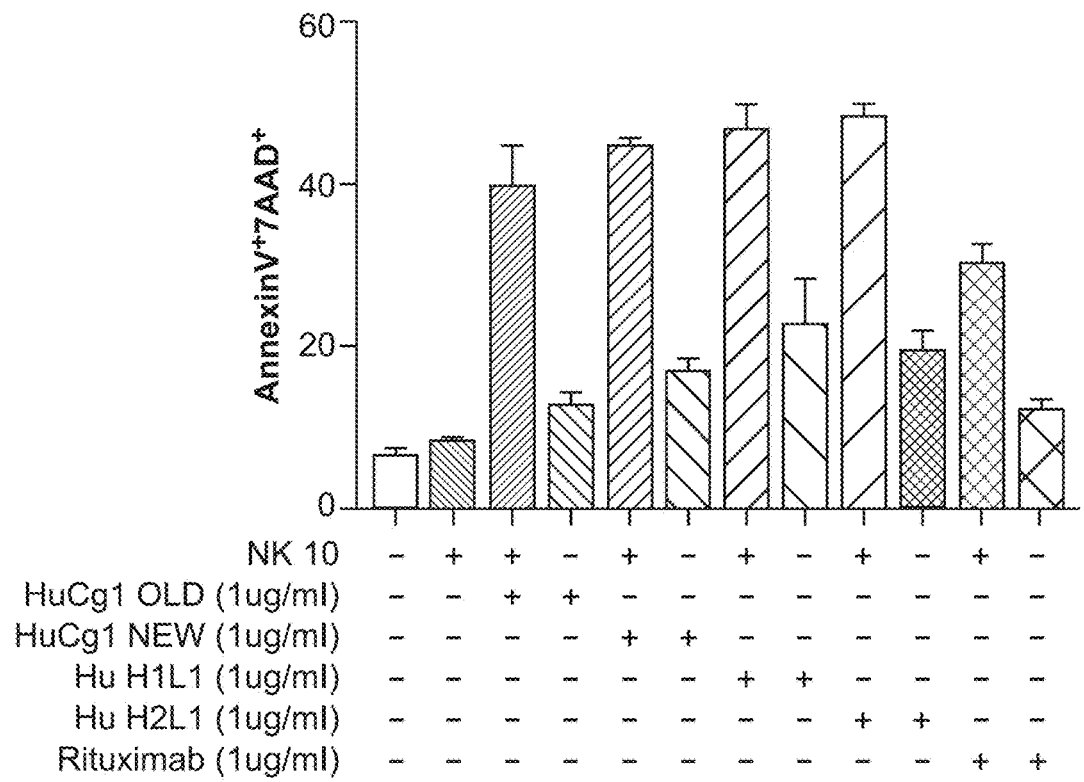
FIG. 5C
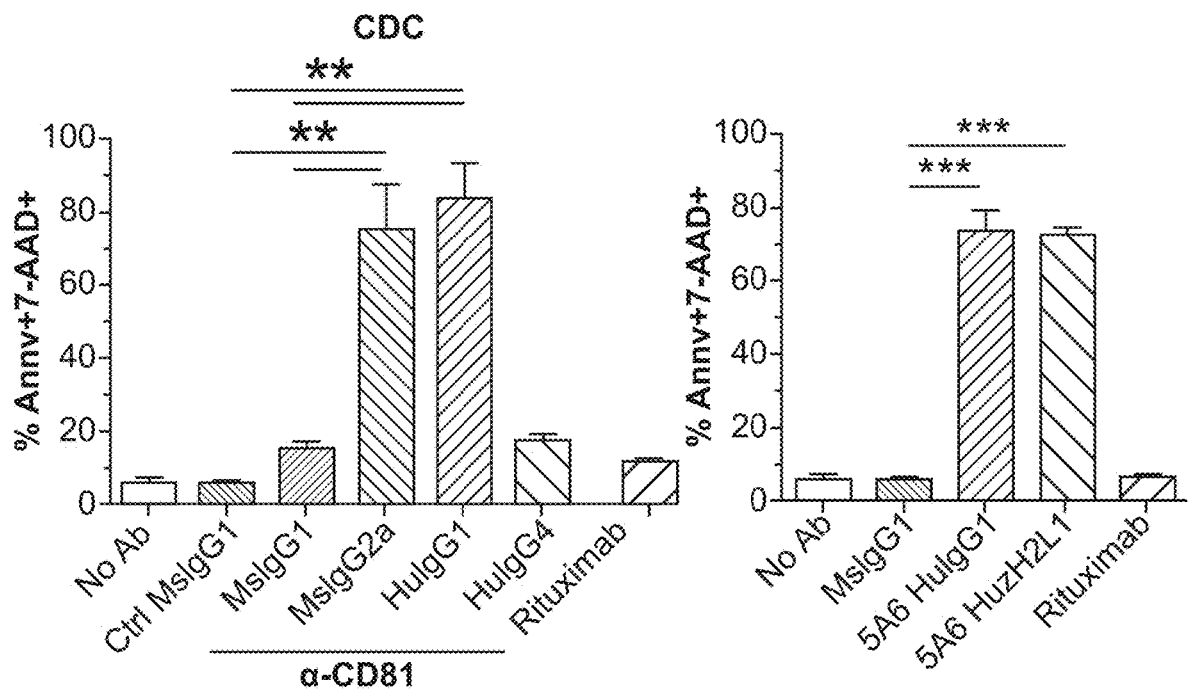
FIG. 6A
FIG. 6B

SEQUENCE LISTING

<160> NUMBER OF SEQ ID NOS: 12

<210> SEQ ID NO 1
<211> LENGTH: 119
<212> TYPE: PRT
<213> ORGANISM: Homo sapiens

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asp Asp
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Ala Ala Thr Tyr Phe Cys
                85                  90                  95

Ala Arg Leu Ser Pro Val Val Val Ile Phe Ile Tyr Trp Gly Gln Gly
            100                 105                 110

Thr Leu Val Thr Val Ser Ala
        115

<210> SEQ ID NO 2
<211> LENGTH: 119
<212> TYPE: PRT
<213> ORGANISM: Homo sapiens

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asp
            20                  25                  30

Ser Ile His Trp Val Arg Gln Ala Pro Gly Gln Gly Leu Glu Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Leu Ser Pro Val Val Val Ile Phe Ile Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Homo sapiens

<400> SEQUENCE: 3

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asp Asp
            20                  25                  30

Ser Ile His Trp Val Lys Gln Ala Pro Gly Gln Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Leu Ser Pro Val Val Val Ile Phe Ile Tyr Trp Gly Gln Gly
                100                 105                 110

Thr Leu Val Thr Val Ser Ser
            115

<210> SEQ ID NO 4
<211> LENGTH: 112
<212> TYPE: PRT
<213> ORGANISM: Homo sapiens

<400> SEQUENCE: 4

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu His Ser
            20                  25                  30

Arg Thr Arg Lys Asn Tyr Leu Ala Trp Phe Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Ala Phe Gly Gly Gly Thr Lys Leu Glu Met Arg
                100                 105                 110

<210> SEQ ID NO 5
<211> LENGTH: 112
<212> TYPE: PRT
<213> ORGANISM: Homo sapiens

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu His Ser
            20                  25                  30

Arg Thr Arg Lys Asn Tyr Leu Ala Trp Tyr Leu Gln Lys Pro Gly Gln
            35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Tyr Asn Leu Tyr Ala Phe Gly Gln Gly Thr Lys Leu Glu Ile Lys
                100                 105                 110

<210> SEQ ID NO 6

<211> LENGTH: 112
<212> TYPE: PRT
<213> ORGANISM: Homo sapiens

<400> SEQUENCE: 6

Asp Ile Val Met Thr Gln Ser Pro Leu Ser Leu Pro Val Thr Pro Gly
1               5                   10                  15

Glu Pro Ala Ser Met Ser Cys Lys Ser Ser Gln Ser Leu Leu His Ser
            20                  25                  30

Arg Thr Arg Lys Asn Tyr Leu Ala Trp Phe Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Ala Val Tyr Tyr Cys Lys Gln
                85                  90                  95

Ser Tyr Asn Leu Tyr Ala Phe Gly Gln Gly Thr Lys Leu Glu Ile Lys
            100                 105                 110

<210> SEQ ID NO 7
<211> LENGTH: 414
<212> TYPE: DNA
<213> ORGANISM: Homo sapiens

<400> SEQUENCE: 7
atggcttggg tggggacctt gctattcctg ctggcagctg cccaaagtat ccaagcacag      60
atccagttgg tgcagtctgg acctgagctg aagaagcctg agagacagt caagatctcc     120 tgcaaggctt ctggttatat cttcacagac gattcaatac actgggtgaa gcaggctccg     180
ggaaagggtt taaagtggat gggctggata acactgaga ctggtgagcc aacatatgca      240
gatgacttca agggacggtt tgccttctct ttggaaacct ctgccagcac tgcctatttg     300
cagatcaaca acctcaaaaa tgaggacgcg gctacatatt tctgtgctag actttccccc     360
gtcgtagtca tctttattta ctggggccaa gggacgctgg tcactgtctc tgca           414

<210> SEQ ID NO 8
<211> LENGTH: 408
<212> TYPE: DNA
<213> ORGANISM: Homo sapiens

<400> SEQUENCE: 8
atgagggctt ggatcttctt tctgctctgc ctggccgggc gcgccttggc ccaggtgcag      60
ctggtgcaat ctgggtctga gttgaagaag cctggggcct cagtgaaggt ttcctgcaag     120
gcttctggat acaccttcac tgacgattca atacactggg tgcgacaggc cctggacaa     180 gggcttgagt ggatgggatg gataaacact gagactggtg agccaacata tgcagatgac     240
ttcaagggac ggtttgtctt ctccttggac acctctgtca gcacggcata tctgcagatc     300
agcagcctaa aggctgagga cactgccgtg tattactgtg cgagactttc ccccgtcgta     360
gtcatcttta tttactgggg ccaaggcacc ctcgttacag tctcctca                  408

<210> SEQ ID NO 9
<211> LENGTH: 408
<212> TYPE: DNA
<213> ORGANISM: Homo sapiens

<400> SEQUENCE: 9

```
atgagggctt ggatcttctt tctgctctgc ctggccgggc gcgccttggc ccagatccag    60
ctggtgcaat ctgggtctga gttgaagaag cctggggcct cagtgaaggt ttcctgcaag   120
gcttctggat acatcttcac tgacgattca atacactggg tgaagcaggc ccctggacaa   180
gggcttaagt ggatgggatg gataaacact gagactggtg agccaacata tgcagatgac   240
ttcaagggac ggtttgcctt ctccttggac acctctgtca gcacggcata tctgcagatc   300
agcagcctaa aggctgagga cactgccgtg tattactgtg cgagactttc ccccgtcgta   360
gtcatcttta tttactgggg ccaaggcacc ctcgttacag tctcctca                408

<210> SEQ ID NO 10
<211> LENGTH: 396
<212> TYPE: DNA
<213> ORGANISM: Homo sapiens

<400> SEQUENCE: 10
atggattcac aggcccaggt tcttatattg ctgctgctat gggtatctgg ttcctgtggg    60
gacattgtga tgtcacagtc tccatcctcc ctggctgtgt cagtaggaga gaaggtcact   120
atgagctgca atccagtca gagtctgctc cacagtagaa cccgaaagaa ctacttggct   180
tggttccagc agaaaccagg gcagtctcct aaactgctga tctactgggc atccactagg   240
gaatctgggg tccctgatcg cttcacaggc agtggatctg gacagatttt cactctcacc   300
atcagcagtg tgcaggctga agacctggca gtttattact gcaagcaatc ttataatctg   360
tacgcgttcg gaggggggac caagctggaa atgaga                             396

<210> SEQ ID NO 11
<211> LENGTH: 387
<212> TYPE: DNA
<213> ORGANISM: Homo sapiens

<400> SEQUENCE: 11
atgagggctt ggatcttctt tctgctctgc ctggccgggc gcgccttggc cgatattgtg    60
atgactcagt ctccactctc cctgcccgtc acccctggag agccggcctc catctcctgc   120
aaatccagtc agagtctgct ccacagtaga acccgaaaga actacttggc ttggtacctg   180
cagaagccag gccagtctcc acagctcctg atctattggg catccactag gaatctgggg   240
gtccctgaca ggttcagtgg cagtggatca ggcacagatt ttacactgaa aatcagcaga   300
gtggaggctg aggatgttgg ggtttattac tgcaagcaat cttataatct gtacgcgttc   360
ggccaaggga caaagttgga aataaaa                                       387

<210> SEQ ID NO 12
<211> LENGTH: 387
<212> TYPE: DNA
<213> ORGANISM: Homo sapiens

<400> SEQUENCE: 12
atgagggctt ggatcttctt tctgctctgc ctggccgggc gcgccttggc cgatattgtg    60
atgactcagt ctccactctc cctgcccgtc acccctggag agccggcctc catgtcctgc   120
aaatccagtc agagtctgct ccacagtaga acccgaaaga actacttggc ttggttccag   180
cagaagccag gccagtctcc aaaactcctg atctattggg catccactag gaatctgggg   240
gtccctgaca ggttcagtgg cagtggatca ggcacagatt ttacactgaa aatcagcaga   300
```

```
gtggaggctg aggatgttgg ggtttattac tgcaagcaat cttataatct gtacgcgttc    360
ggccaaggga caaagttgga aataaaa                                       387
```

HUMANIZED AND CHIMERIC MONOCLONAL ANTIBODIES TO CD81

CROSS REFERENCE

This application claims benefit and is a 371 application of PCT Application No. PCT/US2017/037533, filed Jun. 14, 2017, which claims benefit of U.S. Provisional Patent Application No. 62/351,054, filed Jun. 16, 2016, which applications are incorporated herein by reference in their entirety.

BACKGROUND OF THE INVENTION

CD81 is a tetraspanin molecule, belonging to an evolutionarily conserved family of proteins. All multicellular organisms express members of this family. Tetraspanins are embedded in the plasma membrane by four transmembrane domains that flank short amino and carboxyl cytoplasmic termini and a small and a large extracellular loop (SEL and LEL, respectively). The three dimensional structure of LEL is composed of a stalk of two longer a helices and a novel mushroom-like head structure folded with the help of two disulfide bridges (see Zimmerman et al. (2016) Cell 167(4): 1041-1051.e11). Most anti-CD81 mAbs react with the LEL, as evident by reactivity with recombinant LEL proteins.

Tetraspanins associate with each other in subcellular membrane microdomains, which are dynamic membrane entities that act as signaling platforms. These tetraspanin-enriched microdomains (TEMs) include associated proteins (partner proteins). These partnerships differ in various cell types and in their strength of association. In general, tetraspanin tends to associate with integrins in partnerships that are cell-type specific. Thus, in a cell that expresses several integrins, only one of these integrins might be found in association with a specific tetraspanin molecule. Other partners include members of the immunoglobulin superfamily, such as CD19 and EWI-2, that are frequently associated with tetraspanin molecules.

TEMs facilitate the transmission of extracellular stimuli to intracellular signaling pathways. For example, they enable the recruitment of cytoskeletal actin by activating the ERM family proteins ezrin, radixin, and moesin. In addition, the association of CD81 with EWI-2 was shown to recruit a-actinin to T cell immune synapses. Thus, CD81 embedded in TEMs transmits signals received at the cell membrane to downstream signaling molecules and to adaptor proteins, thereby contributing to specific immune functions. For example, when antigens engage their cognate BCR and simultaneously bind the CD19/CD81/CD21 complex, the threshold for B cell activation is lowered, enhancing downstream signaling events.

Recently, it was shown that expressing exogenous CD81 in a human melanoma cell line enhanced its migrating, invasive, and metastatic abilities in a xenograft model. This and other evidence suggests that CD81 can contribute to tumor cell motility.

In addition to the expression of CD81 on tumor cells, evidence suggests that CD81 modulates host adaptive and innate immune responses. Tumor cells counteract innate and adaptive antitumor immune responses by recruiting regulatory T cells (Treg) and innate myeloid-derived suppressor cells (MDSC), which facilitate immune escape and metastatic dissemination. It has been shown that CD81, while not required for normal development of these cells, is essential for their immunosuppressive function. Modulating the function of CD81 on Tregs and MDSC can provide an important clinical application, as therapies aimed at blocking Treg-T-cell interactions have been shown to reverse tumor-induced immune suppression.

The present invention provides clinically useful anti-CD81 antibodies.

SUMMARY OF THE INVENTION

Compositions and methods are provided relating to humanized or chimeric anti-CD81 monoclonal antibodies. The antibodies of the invention comprise sequences derived from 5A6 monoclonal antibody, bind to human CD81, inhibit invasion of tumor cells and reduce tumor growth and metastasis in the body. Therefore these antibodies find use in various therapeutic methods in the treatment of cancer. Embodiments of the invention include isolated antibodies and derivatives and fragments thereof, pharmaceutical formulations comprising one or more of the humanized or chimeric anti-CD81 monoclonal antibodies; and cell lines that produce these monoclonal antibodies. Also provided are amino acid sequences of the antibodies.

Antibodies of interest include the provided humanized or chimeric antibodies, and variants thereof. The monoclonal antibodies of the invention find particular utility as reagents for the diagnosis and immunotherapy of disease associated with CD81 in humans, particularly in cancer therapy. An advantage of the monoclonal antibodies of the invention derives from the humanization process and use of human Fc regions. Thus, in vivo use of the monoclonal antibodies of the invention for immunotherapy greatly reduces the problems of significant host immune response to the antibodies.

Various forms of the antibodies are contemplated herein. For example, the anti-CD81 antibody may be a full length chimeric or humanized antibody, e.g. having a human immunoglobulin constant region of any isotype, e.g. IgG1, IgG2a, IgG2b, IgG3, IgG4, IgA, etc. or an antibody fragment, e.g. a F(ab')$_2$ fragment, and F(ab) fragment, etc. Fragments comprising CDR regions are also of interest, e.g. for imaging purposes. Furthermore, the antibody may be labeled with a detectable label. Antibodies of the invention may comprise additional amino acid sequences added to the N terminal regions linked by cleavable linkers, which reduce binding to random sites in the body and allow for binding only in sites with tissue enzymes (i.e. tumor cells) that cleave the linker and release the antibody, which is then free to bind to its target antigen. The antibody may be immobilized on a solid phase and/or conjugated with a heterologous compound. The antibody may also be provided as a bi-specific or multispecific antibody reactive with a second antigen, particularly including cancer antigens on immunotherapeutic antigens.

Embodiments of the invention include isolated antibodies and derivatives and fragments thereof that comprise at least one, usually at least 3 CDR sequences as provided herein, usually in combination with framework sequences from a human variable region or as an isolated CDR peptide. In some embodiments an antibody comprises at least one light chain comprising the 3 light chain CDR sequences provided herein situated in a variable region framework, which may be, without limitation, a human or mouse variable region framework, and at least one heavy chain comprising the 3 heavy chain CDR sequence provided herein situated in a variable region framework, which may be, without limitation, a human or mouse variable region framework.

A humanized antibody may comprise as variable regions SEQ ID NO:2 and SEQ ID NO:5, SEQ ID NO:3 and SEQ ID NO:5; SEQ ID NO:2 and SEQ ID NO:6, or SEQ ID NO:3 and SEQ ID NO:6. The heavy constant region, which may be paired with any of SEQ ID NO:1, 2 or 3, may be chosen for efficacy in a desired function, e.g. human IgG1 is shown to improve ADCC in a human effector cell context; and to improve CDC. Mouse IgG2A is shown to improve efficacy in the context of mouse effector cells.

The invention further provides: isolated nucleic acid encoding the antibodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more of the human anti-CD81 antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

Also provided are methods for the treatment of cancer, the methods comprising administering an effective dose or doses of an anti-CD81 antibody of the invention for a period of time sufficient to reduce tumor growth and/or metastasis. In some embodiments the tumor is a CD81 expressing tumor. In other embodiments the tumor does not express CD81, e.g. where the antibody targets Treg and/or MDSC cells of the patient to reduce immune suppression. In some such embodiments the therapy of the invention is combined with one or more additional anti-tumor treatments, e.g. chemotherapy, radiation therapy, surgery, anti-tumor antibodies, immunoregulatory antibodies, and the like.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1. An alignment of sequences for antibodies of the invention.

FIG. 2A Mouse anti-human CD81 monoclonal antibody 5A6 inhibits invasion of human breast cancer cells. A 3D invasion assay demonstrating that anti-human CD81 (SEQ ID NO:1/SEQ ID NO:4 with mouse constant region IgG1) inhibits the invasion of human breast cancer cells (MDA-MB-231) into an extracellular matrix (ECM). Invasion assay images of MDA-MB-231 spheroids were taken at the indicated times. Top panels: ECM containing a mouse IgG1 control antibody; Bottom panels: ECM containing anti-human CD81 (SEQ ID NO:1/SEQ ID NO:4 with mouse constant region IgG1). FIG. 2B Inhibition of invasion is a property of 5A6, other anti-CD81 antibodies do not inhibit invasion of human breast cancer cells. A 3D invasion assay of MDA-MB-231 human breast cancer cells demonstrating that anti-human CD81 (SEQ ID NO:1/SEQ ID NO:4 with mouse constant region IgG1) is unique amongst anti-CD81 Abs in its ability to inhibit invasion of human breast cancer cells (MDA-MB-231) in a 3D invasion assay. Panels: No ECM=breast cancer cell spheroid in the absence of extra cellular matrix, IC=ECM embedded with a control mouse IgG1 antibody (isotype control), 5A6=ECM embedded with anti-human CD81 (SEQ ID NO:1/SEQ ID NO:4 with mouse constant region IgG1), 1D6, JS81 and 1.3.3.22=ECM embedded with the indicated anti-human CD81 antibodies with mouse constant region IgG1. Bargraphs depict the invasion areas of the indicated anti-human CD81 antibodies and controls.t test ***p value=0.0001.

FIG. 3A Mouse anti-human CD81 monoclonal antibody 5A6 prolongs survival of SCID mice challenged with a human B cell lymphoma (Raji). Human B cell lymphoma expressing luciferase (Raji-Luc) were injected into SCID mice ($1.5 \times 10^6$/mouse), tumors were treated with 100 μg of mouse anti-human CD81 mAb (SEQ ID NO:1/SEQ ID NO:4 with mouse constant region IgG1), with 100 μg of a control mouse IgG1, and with 100 μg Rituximab weekly x4. Tumors were visualized by bioluminescene, shown are day 23 imaging (after receiving 2 doses of the antibodies). Survival of mice shows similar efficacy of treatment by the mouse anti-human CD81 (SEQ ID NO:1/SEQ ID NO:4 with mouse constant region IgG1) and by Rituximab (human contant region IgG1). Log-rank test 5A6 vs. control mouse IgG1 *p value=0.0001; Rituximab vs. control mouse IgG1 *p value=0.0002. FIG. 3B Switching the constant region enhances the therapeutic efficacy of 5A6 and chimeric anti-human CD81 antibodies, better protecting SCID mice from a challenge with a human B cell lymphoma (Raji) than Rituximab. Human B cell lymphoma expressing luciferase (Raji-Luc) were injected into SCID mice ($1.5 \times 10^6$/mouse). Tumors were treated weekly x4 with 100 μg of anti-human CD81 mAb (SEQ ID NO:1/SEQ ID NO:4 with mouse constant region IgG1 or IgG2a, or with human light chain constant region kappa and human heavy chain constant regions IgG1 or IgG4). Controls groups received 100 μg weekly x3 of mouse IgG1 (MsIgG1) or Rituximab (human constant region IgG1). Tumors visualized by bioluminescence on day 22 show superiority of treatment by the mouse anti-human CD81 I (SEQ ID NO:1/SEQ ID NO:4 with mouse constant region IgG2a), followed by that of the chimeric 5A6 antibody (SEQ ID NO:1/SEQ ID NO:4 with human heavy chain constant region IgG1 and human light chain region Kappa). t test *p=value 0.149.

FIG. 4A-4B. FIG. 4A Mouse anti-human CD81 monoclonal antibody 5A6 reduces human breast cancer metastases in a xenograft model. Human breast cancer cells (MDA-MB-231) were injected in matrigel into the mammary pads of SCID mice ($2.5 \times 10^6$/mouse). Mice were treated weekly for 4 weeks with 100 μg of anti-human CD81 mAb (SEQ ID NO:1/SEQ ID NO:4 with mouse constant region IgG1), or with a control mouse IgG1 mAb starting on day 7 post tumor inoculation. Mice were sacrificed on day 75, lungs were inflated and injected with India ink to visualize tumor metastases (seen as white spots). Left: lung obtained from a mouse treated with the control mAb, right: lung obtained from a mouse treated with the anti-human CD81 mAb (SEQ ID NO:1/SEQ ID NO:4 with mouse constant region IgG1). FIG. 4B Switching the constant region of 5A6 reduces tumor growth and metastases in SCID mice challenged with human breast cancer cells. Cells of a more aggressive clone of human breast cancer MDA-MB-231, expressing luciferase (MDA-MB-231-Luc) were injected in matrigel into the mammary pads of SCID mice ($1.5 \times 10^6$/mouse). Mice were treated weekly for 3 weeks with 100 μg of anti-human CD81 mAb (SEQ ID NO:1/SEQ ID NO:4 with mouse constant regions IgG, with (SEQ ID NO:1/SEQ ID NO:4 with mouse constant regions IgG2a), or with a control mouse IgG1 mAb starting on day 7 post tumor inoculation (as illustrated in the upper panel). Tumor volumes were measured every other day (shown on day 23, bottom left panel). Mice were sacrificed on day 26, and metastases in lungs, livers and spleens were measured using bioluminescence imaging. The IgG2a isotype of 5A6 mouse anti-human CD81 (SEQ ID NO:1/SEQ ID NO:4 with mouse constant region IgG2a) was most effective in reducing tumor growth (left lower panel) and metastases to lungs, livers and spleens. t test *p value=0.01, **p value=0.0023.

FIG. 5A-5C. FIG. 5A Mouse anti-human CD81 antibody 5A6 better mediates antibody-dependent cell cytotoxicity (ADCC) than other anti-human CD81 antibodies, 5A6 is also better than other anti-human CD81 antibodies and Rituximab in direct killing of Raji cells. Anti-human CD81 (SEQ ID NO:1/SEQ ID NO:4 with mouse constant region IgG1) is unique amongst anti-CD81 antibodies in its ability to mediate ADCC of human B cell lymphoma (Raji). Direct killing by anti-human CD81 (SEQ ID NO:1/SEQ ID NO:4 with mouse constant region IgG1) is superior to that of both Rituximab and other anti-human CD81 antibodies. Raji cells were incubated overnight with 1 μg/ml of the indicated mAb alone, or in the presence of purified human NK cells (NK:Raji 5:1), cell death was quantified by AnnexinV/7AAD positivity. t test *p value=0.034, ***p value=0.000. FIG. 5B Switching the constant region of 5A6 to that of human IgG1 increases antibody-dependent cell cytotoxicity (ADCC). Chimeric anti-human CD81 mAb (SEQ ID NO:1/SEQ ID NO:4 with human heavy chain constant region IgG1 and human light chain region Kappa) is more effective than mouse anti-human CD81 mAb (SEQ ID NO:1/SEQ ID NO:4 with mouse constant region IgG1), it is also more effective than Rituximab in NK cell-mediated antibody dependent cell cytotoxicity (ADCC). Raji cells were incubated overnight with 0.5 μg/ml of the indicated mAb alone, or in the presence of purified human NK cells (NK:Raji 2:1), cell death was quantified by AnnexinV/7AAD positivity. FIG. 5C Humanized anti-human CD81 antibodies better mediate ADCC and direct killing of Raji cells than Rituximab. Humanized anti-human CD81 mAbs (H1L1 SEQ ID NO:2/SEQ ID NO:5 with human heavy chain constant region IgG1 and human light chain region Kappa) and H2L1 (SEQ ID NO:3/SEQ ID NO:5 with human heavy chain constant region IgG1 and human light chain region Kappa) are as effective as chimeric anti-human CD81 mAb (SEQ ID NO:1/SEQ ID NO:4 with human heavy chain constant region IgG1 and and human light chain region Kappa). Chimeric anti-human CD81 mAb mediate ADCC independent of batch product. The humanized and chimerized anti-human CD81 are more effective than Rituximab in mediating ADCC and in direct killing of Raji cells. Raji cells were incubated overnight with 1 μg/ml of the indicated mAb alone, or in the presence of purified human NK cells (NK:Raji 10:1), cell death was quantified by AnnexinV/7AAD positivity.

FIG. 6A-6B. FIG. 6A Complement dependent cytotoxicity mediated by mouse anti-human CD81 IgG1 antibody is highly augmented by switching the constant region to that of the mouse IgG2a and by chimerizing the antibody using the human IgG1 constant region. Mouse anti-human CD81 antibodies MSIgG2a (SEQ ID NO:1/SEQ ID NO:4 with mouse constant region IgG2a) and chimeric HuIgG1 (SEQ ID NO:1/SEQ ID NO:4 with human heavy chain constant region IgG1 and human light chain constant region kappa ) highly augment complement dependent cytotoxicity (CDC). By contrast, anti-human CD81 MsIG1 (SEQ ID NO:1/SEQ ID NO:4 with mouse constant region IgG1) and chimeric HuIgG4 (SEQ ID NO:1/SEQ ID NO:4 with human heavy chain constant region IgG4 and human light chain constant region kappa ) as well Rituximab poorly mediate CDC. t test p value=0.0051 MsIgG1 vs 5A6 MsIgG2a,  p value=0.0015 MsIgG1 vs 5A6 HuIgG1. FIG. 6B Complement dependent cytotoxicity mediated by chimerized anti-human CD81 IgG1 and by humanized anti-human CD81 IgG1 antibodies are highly superior to that of mouse anti-human CD81 IgG1. Chimeric HuIgG1 (SEQ ID NO:1/SEQ ID NO:4 with human heavy chain constant region IgG1 and human light chain constant region kappa) and the humanized anti-CD81 antibody (SEQ ID NO:3/SEQ ID NO:5 with human heavy chain constant region IgG1 and human light chain constant region kappa) are superior mediators of CDC by comparison to mouse anti-human CD81 antibody MSIgG1 (SEQ ID NO:1/SEQ ID NO:4 with mouse constant region IgG1) and to Rituximab. t test p*** value=0.0001.

FIG. 7A Raji cells are more effective than PBMC (derived from a healthy donor) at binding mouse anti-human CD81 antibody 5A6, especially at lower antibody concentrations, and are more sensitive to anti-CD81-mediated CDC even when present at a 1:1000 ratio. To determine the relative binding of mouse anti-human CD81 (SEQ ID NO:1/SEQ ID NO:4 with mouse constant region IgG1) to PBMCs vs. Raji cells, PBMC were labeled with violet tracking dye (VTD) and Raji cells with carboxyfluorescein succinimidyl ester (CFSE) and mixed at 1:1 ratio. Serial dilutions of the antibody were then added to the mixed cells. As seen in the cell-binding assay (left panel) the antibody bound to Raji cells at low concentrations, whereas PBMC bind only at the higher antibody concentrations. To determine the sensitivity of PBMCs vs. Raji cells to CDC-mediated killing by mouse anti-human CD81 (SEQ ID NO:1/SEQ ID NO:4 with mouse constant region IgG1), PBMC were labeled with VTD and Raji cells with CFSE and mixed at increasing ratios of PBMC to Raji cells. At a mixture of 1:1 the antibody killed 90% of Raji cells, but only 6% of PBMC (middle panels). Remarkably, Raji cells were more sensitive to anti-CD81 mediated CDC, even when present at a 1:1000 ratio to PBMC (right panel). FIG. 7B Patient-derived lymphoma B cells are more sensitive to CD81-mediated CDC than normal T cells present in the same biopsy specimen. CD81 is expressed on follicular lymphoma (FL) tumor B cells, as well as on normal T cells within biopsies of FL samples. Shown are histograms of CD81 expression on B and T cells of 3 FL biopsy specimens and on a healthy donor (HD) PBMC. CDC mediated killing by mouse anti-human CD81 antibody (SEQ ID NO:1/SEQ ID NO:4 with mouse constant region IgG2a) on tumor B and normal T cells of the same FL patient reveals that tumor B cells are more sensitive than normal T cells to 5A6-mediated killing. The same results were obtained using the chimeric anti-human CD81 antibody (SEQ ID NO:1/SEQ ID NO:4 with human heavy chain constant region IgG1 and human light chain constant region kappa). B cells (squares), T cells (triangles).

DETAILED DESCRIPTION OF THE INVENTION

Figure 2A:
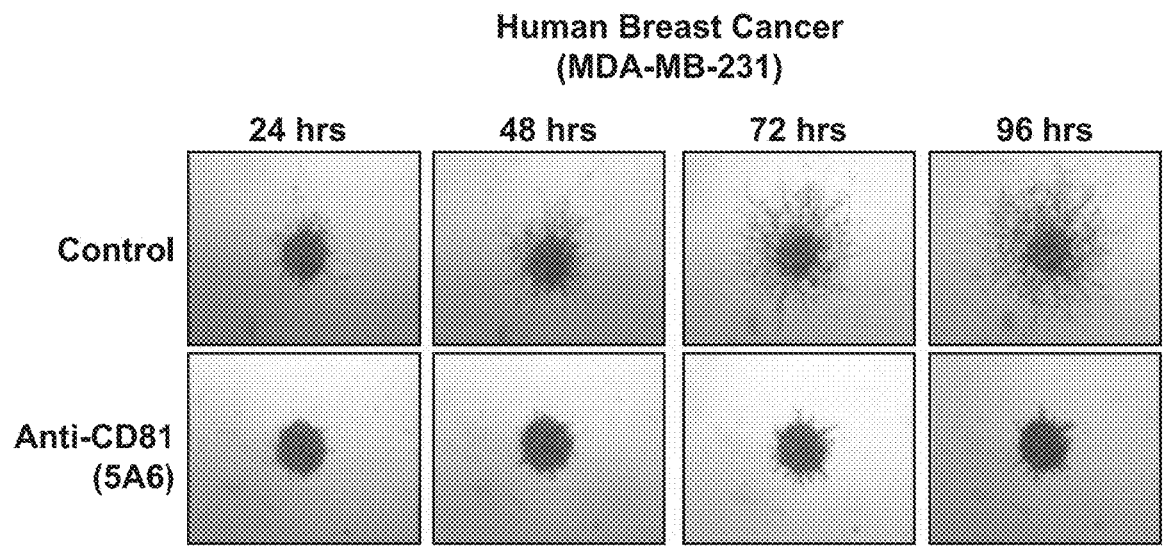
FIG. 2A-2B.

The present invention relates to humanized monoclonal antibodies which are specific for CD81. Also disclosed is a nucleic acid, and amino acid sequence of such antibodies. The antibodies find use in therapeutic and diagnostic methods associated with CD81.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Antibodies of the invention may have an Fc sequence with enhanced effector functions, e.g. by increasing their binding capacities to FcγRIIIA and increasing ADCC activity. For example, fucose attached to the N-linked glycan at Asn-297 of Fc sterically hinders the interaction of Fc with FcγRIIIA, and removal of fucose by glyco-engineering can increase the binding to FcγRIIIA, which translates into >50-fold higher ADCC activity compared with wild type IgG1 controls. Protein engineering, through amino acid mutations in the Fc portion of IgG1, has generated multiple variants that increase the affinity of Fc binding to FcγRIIIA. Notably, the triple alanine mutant S298A/E333A/K334A displays 2-fold increase binding to FcγRIIIA and ADCC function. S239D/I332E (2×) and S239D/I332E/A330L (3×) variants have a significant increase in binding affinity to FcγRIIIA and augmentation of ADCC capacity in vitro and in vivo. Other Fc variants identified by yeast display also showed the improved binding to FcγRIIIA and enhanced tumor cell killing in mouse xenograft models. See, for example Liu et al. (2014) JBC 289(6):3571-90, herein specifically incorporated by reference.

The CDR sequences of exemplary anti-CD81 heavy and light chains combinations are set forth in the sequence listing, and shown in FIG. 1, where exemplary CDR regions are underlined. In some embodiments the set of CDR sequences are provided in a variable region of SEQ ID NO:1, 2 or 3 for heavy chain; and SEQ ID NO:4, 5 or 6 for the light chain. In some embodiments the CDR sequences are maintained in a combination, i.e. a humanized antibody will comprise both heavy chain CDR sequences and light chain CDR sequences.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, $IgA_2$. The heavy-chain constant domains that correspond to the different classes of immunoglobulins are called α, δ, ε, γ, and μ, respectively. The subunit structures and three-dimensional configurations of different classes of immunoglobulins are well known. In some embodiments of the invention, the heavy chain constant region is selected to provide for high ADCC activity, including without limitation human IgG1. In other embodiments a low ADCC activity may be selected, e.g. with human IgG4, or with a "dead" Fc in which effector functions are absent or reduced.

Other Fc variants are possible, including without limitation one in which a region capable of forming a disulfide bond is deleted, or in which certain amino acid residues are eliminated at the N-terminal end of a native Fc form or a methionine residue is added thereto. Thus, in one embodiment of the invention, one or more Fc portions of the scFc molecule can comprise one or more mutations in the hinge region to eliminate disulfide bonding. In yet another embodiment, the hinge region of an Fc can be removed entirely. In still another embodiment, the scFc molecule can comprise an Fc variant.

Further, an Fc variant can be constructed to remove or substantially reduce effector functions by substituting, deleting or adding amino acid residues to effect complement binding or Fc receptor binding. For example, and not limitation, a deletion may occur in a complement-binding site, such as a C1q-binding site. Techniques of preparing such sequence derivatives of the immunoglobulin Fc fragment are disclosed in International Patent Publication Nos. WO 97/34631 and WO 96/32478. In addition, the Fc domain may be modified by phosphorylation, sulfation, acrylation, glycosylation, methylation, farnesylation, acetylation, amidation, and the like.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-CD81 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, $F(ab')_2$, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. In some embodiments a chimeric antibody comprises a mouse variable region, e.g. as set forth in SEQ ID NO:1 and SEQ ID NO:4, fused to a human constant region sequence.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-CD81 antibody fused to an "epitope tag". The epitope tag polypeptide has enough residues to provide an epitope against which an antibody can be made, yet is short enough such that it does not interfere with activity of the CD81 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)).

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Polypeptides

In one aspect, the present invention is directed to humanized or chimeric monoclonal antibodies that are specifically reactive with CD81, and cell lines that produce such antibodies. Variable regions of exemplary antibodies are provided. Antibodies of interest include these provided combinations, as well as fusions of the variable regions to appropriate constant regions or fragments of constant regions, e.g. to generate F(ab)' antibodies. Variable regions of interest include at least one CDR sequence of the provided anti-CD81 antibody, where a CDR may be 3, 4, 5, 6, 7, 8, 9, 10, 11, 12 or more amino acids. Alternatively, antibodies of interest include a variable region as set forth in the provided antibodies, or pairs of variable regions sequences as set forth herein.

Variable regions of interest include at least one CDR sequence from the variable regions provided herein, usually at least 2 CDR sequences, and more usually 3 CDR sequences. An exemplary CDR designation is shown in FIG. 1, corresponding to the underlined residues above, however one of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342:877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlan et al. "Identification of specificity-determining residues in antibodies." Faseb J. 1995; 9:133-139, each of which is herein specifically incorporated by reference.

In some embodiments a polypeptide of interest has a contiguous sequence of at least about 10 amino acids, at least about 15 amino acids, at least about 20 amino acids, at least about 25 amino acids, at least about 30 amino acids, up to the complete provided variable region set forth in any of SEQ ID NO:1, 2, 3, 4, 5 and 6. Polypeptides of interest also include variable regions sequences that differ by up to one, up to two, up to 3, up to 4, up to 5, up to 6 or more amino acids as compared to the amino acids sequence set forth herein. In other embodiments a polypeptide of interest is at least about 80%, at least about 85%, at least about 90%, at least about 95%, at least about 99% identical to the amino acid sequence set forth herein.

In addition to Fabs, smaller antibody fragments and epitope-binding peptides having binding specificity for at least one epitope of CD81 are also contemplated by the present invention and can also be used in the methods of the invention. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escherichia coli*," Nature 341: 644-646, disclose a method for screening to obtain an antibody heavy chain variable region (H single domain antibody) with sufficient affinity for its target epitope to bind thereto in isolate form.

The invention also provides isolated nucleic acids encoding the humanized or chimeric anti-CD81 antibodies, vectors and host cells comprising the nucleic acid, and recombinant techniques for the production of the antibody. Nucleic acids of interest may be at least about 80% identical to the provided nucleic acid sequences, at least about 85%, at least about 90%, at least about 95%, at least about 99%, or identical. In some embodiments a contiguous nucleotide sequence encoding a polypeptide of any one of SEQ ID NO:1-6 of at least about 20 nt., at least about 25 nt, at least about 50 nt., at least about 75 nt, at least about 100 nt, and up to the complete provided sequence may be used. Such contiguous sequences may encode a CDR sequence, or may encode a complete variable region. As is known in the art, a variable region sequence may be fused to any appropriate constant region sequence.

For recombinant production of the antibody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The anti-CD81 antibody of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for anti-CD81 antibody production and cultured in conventional nutrient media modified as appropriate for inducing promoters, selecting transformants, or amplifying the genes encoding the desired sequences.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human yl, γ2, or γ4 heavy chains (Lindmark et al., J. Immunol. Meth. 62:1-13 (1983)). Protein G is recommended for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The humanized or chimeric monoclonal antibodies of the invention can be used in the treatment of cancer, including in a combination therapy with additional immunotherapeutic agents e.g. as a combination of two or more antibodies; or as a bispecific or other multispecific modality. The invention provides a wide variety of mono-specific and multi-specific, including without limitation bispecific, antibody configurations, which comprise a CD81-binding antibody of the invention. In some such embodiments, a second antigen binding region is included. In some embodiments the second antigen binding region specifically binds to a tumor antigen. In some embodiments the second antigen binding region specifically binds to an immune checkpoint protein.

In some embodiments, a method is provided for treatment of cancer, the method comprising administering to an individual in need thereof an effective dose of a mono-specific, bi-specific, etc. antibody of the invention. Where the antibody is bispecific, a second antigen-binding site may specifically bind a tumor antigen, a checkpoint protein, etc. In various embodiments, the cancer is selected from the group consisting of ovarian cancer, breast cancer, gastrointestinal, brain cancer, head and neck cancer, prostate cancer, colon cancer, lung cancer, leukemia, lymphoma, sarcoma, carcinoma, neural cell tumors, squamous cell carcinomas, germ cell tumors, metastases, undifferentiated tumors, seminomas, melanomas, myelomas, neuroblastomas, mixed cell tumors, and neoplasias caused by infectious agents.

Many tumor cells produce antigens, which may be released in the bloodstream or remain on the cell surface.

Antigens have been identified in most of the human cancers, including Burkitt lymphoma, neuroblastoma, malignant melanoma, osteosarcoma, renal cell carcinoma, breast carcinoma, prostate cancer, lung carcinomas, and colon cancer. A key role of the immune system is detection of these antigens to permit subsequent targeting for eradication. However, despite their foreign structure, the immune response to tumor antigens varies and is often insufficient to prevent tumor growth.

Tumor-associated antigens (TAAs) are relatively restricted to tumor cells, whereas tumor-specific antigens (TSAs) are unique to tumor cells. TSAs and TAAs typically are portions of intracellular molecules expressed on the cell surface as part of the major histocompatibility complex.

Tissue specific differentiation antigens are molecules present on tumor cells and their normal cell counterparts. Tumor-associated antigens known to be recognized by therapeutic mAbs fall into several different categories. Hematopoietic differentiation antigens are glycoproteins that are usually associated with cluster of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA, epidermal growth factor receptor (EGFR; also known as ERBB1)' ERBB2 (also known as HER2), ERBB3, MET (also known as HGFR), insulin-like growth factor 1 receptor (IGF1R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11). Antigens involved in angiogenesis are usually proteins or growth factors that support the formation of new microvasculature, including vascular endothelial growth factor (VEGF), VEGF receptor (VEGFR), integrin $\alpha V\beta 3$ and integrin $\alpha 5\beta 1$. Tumor stroma and the extracellular matrix are indispensable support structures for a tumor. Stromal and extracellular matrix antigens that are therapeutic targets include fibroblast activation protein (FAP) and tenascin.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD1 are PD1 ligand 1 (PDL1; also known as B7-H1 and CD274) and PDL2 (also known as B7-DC and CD273). PDL1 is expressed on cancer cells and through binding to its receptor PD1 on T cells it inhibits T cell activation/function.

Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR) and the family of killer inhibitory receptors have each been associated with the inhibition of lymphocyte activity and in some cases the induction of lymphocyte anergy. Antibody targeting of these receptors can be used in the methods of the invention.

Agents that agonize an immune costimulatory molecule are also useful in the methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages.

Anti CCR4 (CD194) antibodies of interest include humanized monoclonal antibodies directed against C—C chemokine receptor 4 (CCR4) with potential anti-inflammatory and antineoplastic activities. CCR2 is expressed on inflammatory macrophages that can be found in various inflammatory conditions, e.g. rheumatoid arthritis; and have also been identified as expressed on tumor promoting macrophages. CCR2 is also expressed on regulatory T cells, and the CCR2 ligand, CCL2, mediates recruitment of regulatory T cells into tumors. Regulatory T cells suppress a response for anti-tumor T cells and thus their inhibition or depletion is desired.

As a matter of convenience, the antibody or combination of antibodies of the present invention can be provided in a kit, i.e., a packaged combination of reagents in predetermined amounts with instructions for therapeutic use. In addition, other additives may be included such as stabilizers, buffers and the like. Particularly, the antibodies may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD81 associated disease.

The therapeutic dose may be at least about 0.01 µg/kg body weight, at least about 0.05 g/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The anti-CD81 antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-CD81 antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-CD81 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Cloning and Generation of Monoclonal Antibodies Directed Against Human CD81

Antibodies of the invention include mouse variable regions, e.g. heavy chain SEQ ID NO:1 and light chain SEQ ID NO:4 that can be produced as a chimera with a human constant region; e.g. paired with each other, or paired with a humanized variable region of the invention. Humanized heavy chain variable regions include those set forth in SEQ ID NO:2 and SEQ ID NO:3, which can be paired with any of the light chain variable regions provided herein. Humanized light chain variable regions include those set forth in SEQ ID NO:5 and SEQ ID NO:6, which can be paired with any of the heavy chain variable regions provided herein. (exemplary CDR sequences are underlined).

(SEQ ID NO: 1)
QIQLVQSGPELKKPGETVKISCKASGYIFT<u>DDSIHW</u>VKQAPGKGLKWMG<u>W
INTETGEPTYADDFKGR</u>FAFSLETSASTAYLQINNLKNEDAATYFCAR<u>LS
PVVVIFIY</u>WGQGTLVTVSA

Figure 2B:
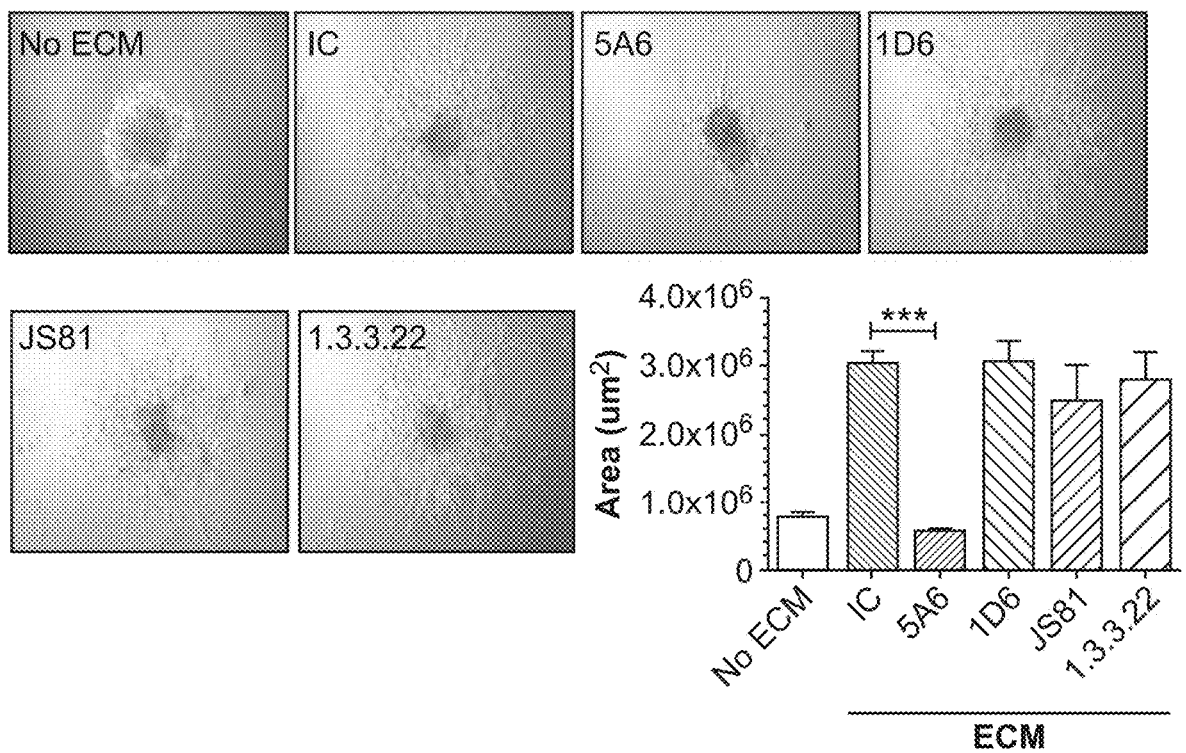

-continued (SEQ ID NO: 2)
QVQLVQSGSELKKPGASVKVSCKASGYTFT<u>DDSIH</u>WVRQAPGQGLEWMG<u>W
INTETGEPTYADDFKG</u>RFVFSLDTSVSTAYLQISSLKAEDTAVYYCAR<u>LS
PVVVIFIY</u>WGQGTLVTVSS (SEQ ID NO: 3)
QIQLVQSGSELKKPGASVKVSCKASGYIFT<u>DDSIH</u>WVKQAPGQGLKWMG<u>W
INTETGEPTYADDFKG</u>RFAFSLDTSVSTAYLQISSLKAEDTAVYYCAR<u>LS
PVVVIFIY</u>WGQGTLVTVSS (SEQ ID NO: 4)
DIVMSQSPSSLAVSVGEKVTMSC<u>KSSQSLLHSRTRKNYLA</u>WFQQKPGQSP
KLLIY<u>WASTRES</u>GVPDRFTGSGSGTDFTLTISSVQAEDLAVYYC<u>KQSYNL
YA</u>FGGGTKLEMR (SEQ ID NO: 5)
DIVMTQSPLSLPVTPGEPASISC<u>KSSQSLLHSRTRKNYLA</u>WYLQKPGQSP
QLLIY<u>WASTRES</u>GVPDRFSGSGSGTDFTLKISRVEAEDVGVYYC<u>KQSYNL
YA</u>FGQGTKLEIK (SEQ ID NO: 6)
DIVMTQSPLSLPVTPGEPASMSC<u>KSSQSLLHSRTRKNYLA</u>WFQQKPGQSP
KLLIY<u>WASTRES</u>GVPDRFSGSGSGTDFTLKISRVEAEDLAVYYC<u>KQSYNL
YA</u>FGQGTKLEIK Functional Analysis A 3D invasion assay was used to determine the effectiveness of anti-CD81 antibodies in the inhibition of invasiveness of human breast cancer cells (MDA-MB-231) into an extracellular matrix (ECM). Data shown in FIG. 2A and FIG. 2B. Invasion assay images of MDA-MB-231 spheroids were taken at the indicated times. The mouse anti-human antibody (SEQ ID NO:1/SEQ ID NO:4 with mouse constant region IgG1) inhibits the invasion of human breast cancer cells. Shown in FIG. 2B, the effect is specific for the 5A6 antibody and other anti-CD81 antibodies do not inhibit invasion of human breast cancer cells.

Figure 3A:
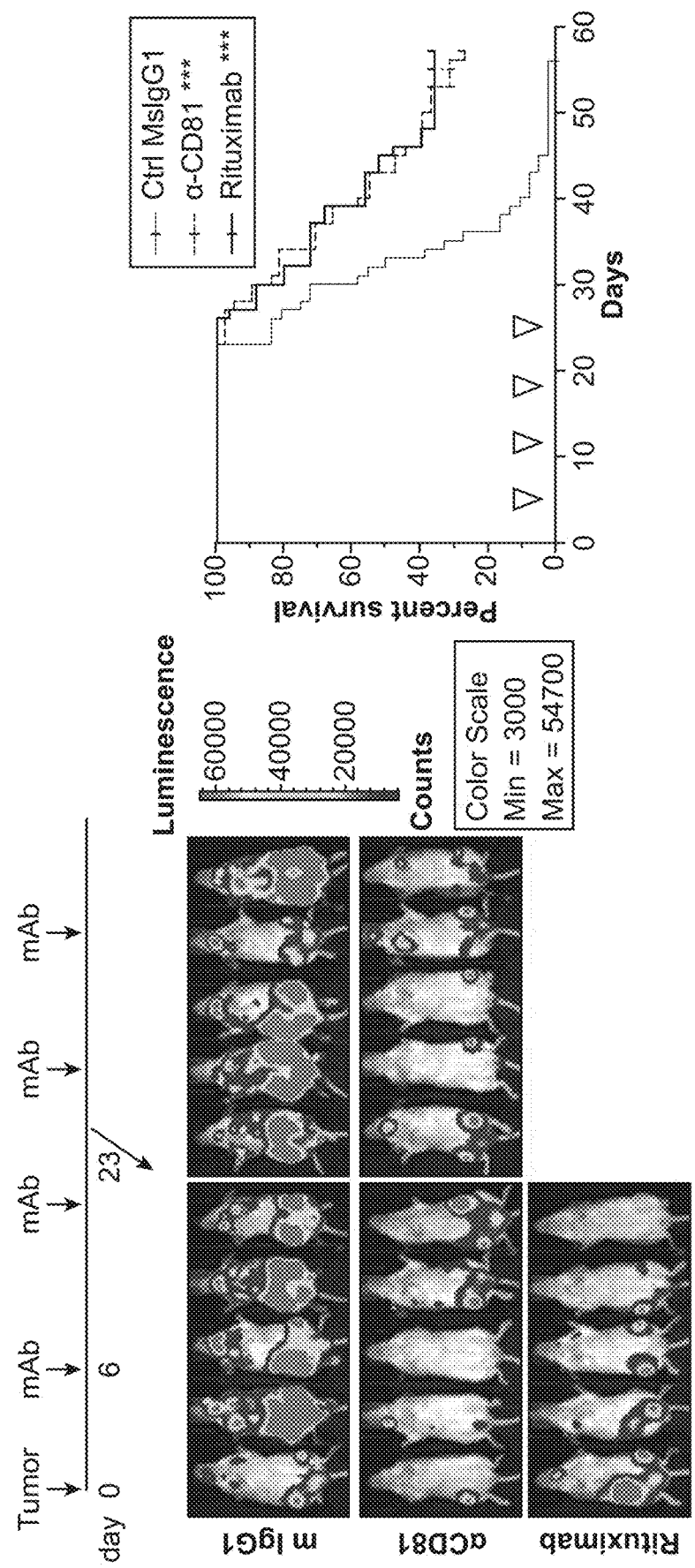
FIG. 3A-3B.
Figure 3B:
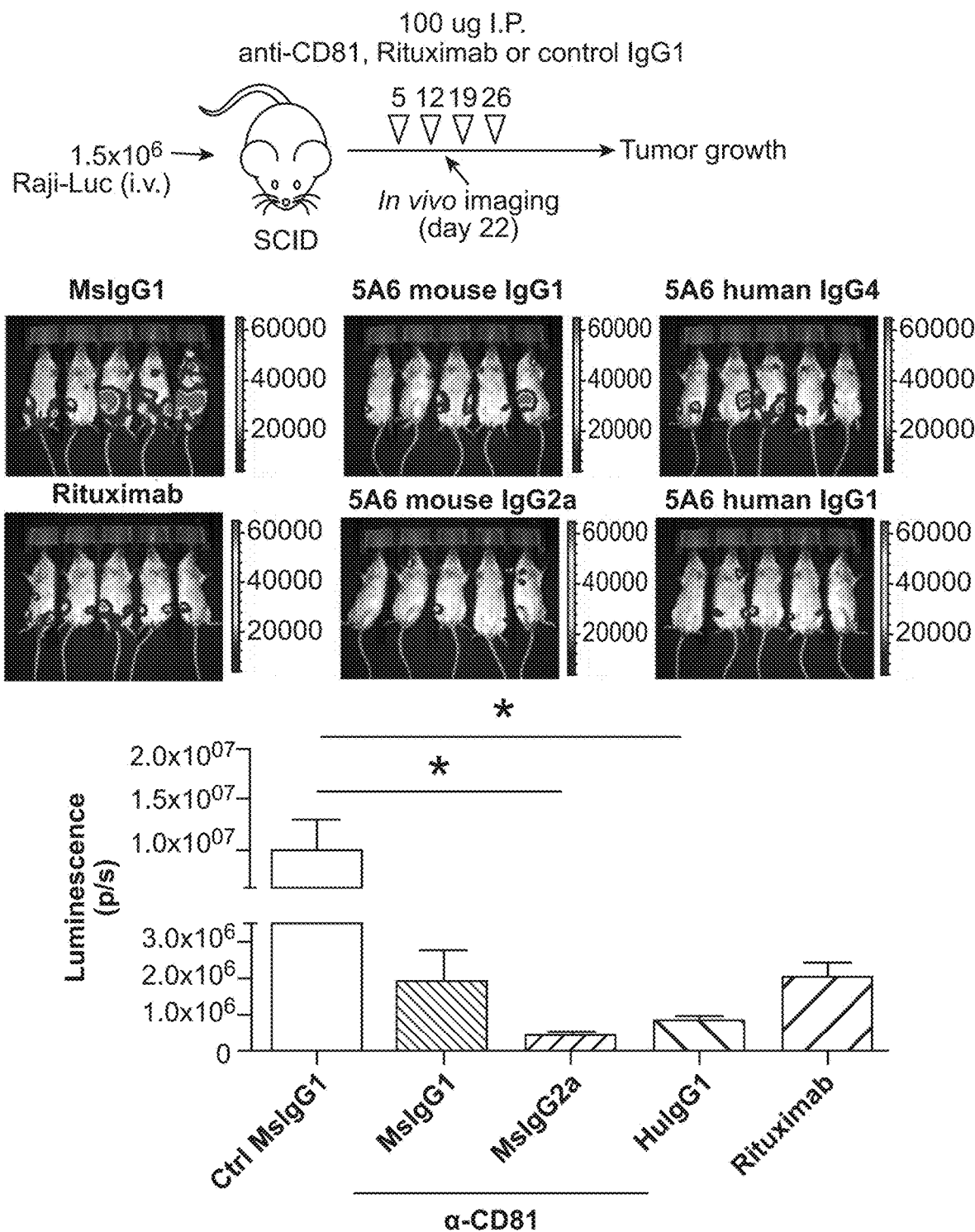

An in vivo xenograft model was used to assess the antibody effectiveness in the context of mouse effector cells. The mouse anti-human CD81 monoclonal antibody prolonged survival of a SCID mouse challenged with a human B cell lymphoma (Raji), as shown in FIG. 3A. Tumors were treated with 100 µg of mouse anti-human CD81 mAb (SEQ ID NO:1/SEQ ID NO:4 with mouse constant region IgG1), with 100 µg of a control mouse IgG1, and with 100 µg Rituximab weekly ×4. The survival was similar for treatment with the anti-CD81 antibody and with Rituximab. It was further shown (see FIG. 3B) that in this context of mouse effector cells, switching the constant region from mouse IgG1 to mouse IgG2a enhanced the therapeutic efficacy of 5A6 and chimeric anti-human CD81 antibodies.

In a xenograft model for metastasis, mouse anti-human CD81 monoclonal antibody 5A6 reduced human breast cancer metastases in a xenograft model (shown in FIG. 4A). Human breast cancer cells (MDA-MB-231) were injected in matrigel into the mammary pads of SCID mice (2.5×10⁶/mouse). Mice were treated weekly for 4 weeks with 100 µg of anti-human CD81 mAb (SEQ ID NO:1/SEQ ID NO:4 with mouse constant region IgG1), or with a control mouse IgG1 mAb starting on day 7 post tumor inoculation. It was further shown (see FIG. 4B) that in this context of mouse effector cells, switching the constant region from mouse IgG1 to mouse IgG2a enhanced the therapeutic efficacy in reducing tumor growth and metastasis of 5A6 and chimeric anti-human CD81 antibodies.

Figure 5A:
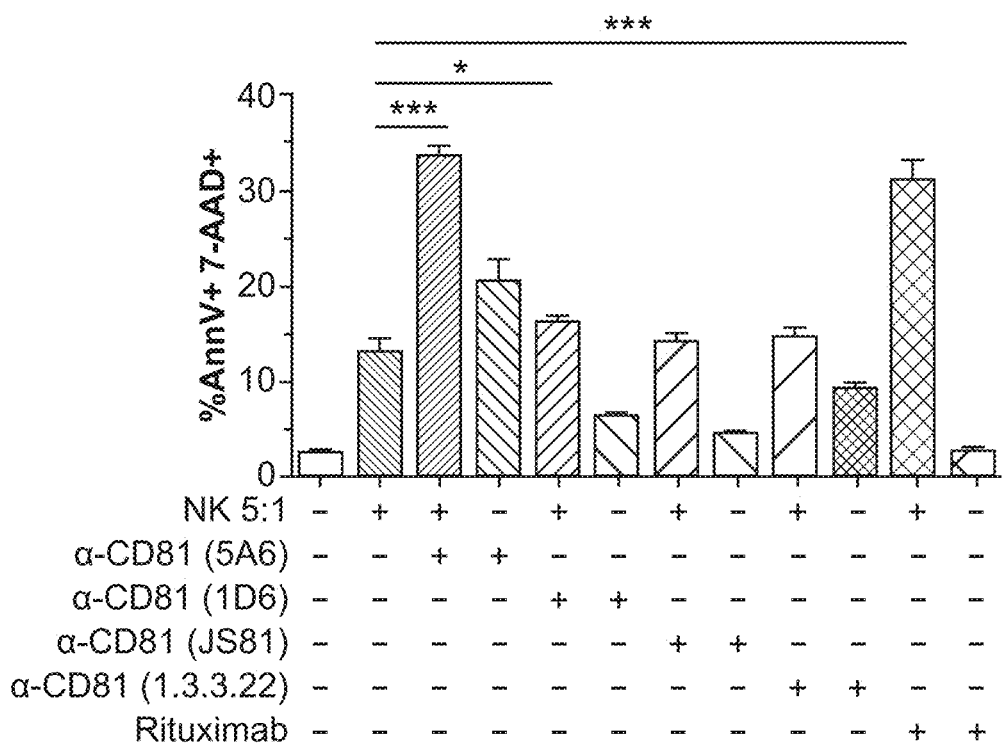

Mouse anti-human CD81 antibody 5A6 better mediates antibody-dependent cell cytotoxicity (ADCC) than other anti-human CD81 antibodies, 5A6 is also better than other anti-human CD81 antibodies and Rituximab in direct killing of Raji cells, shown in FIG. 5A. Anti-human CD81 (SEQ ID NO:1/SEQ ID NO:4) was unique amongst anti-CD81 antibodies in its ability to mediate ADCC of human B cell lymphoma (Raji).

Figure 5B:
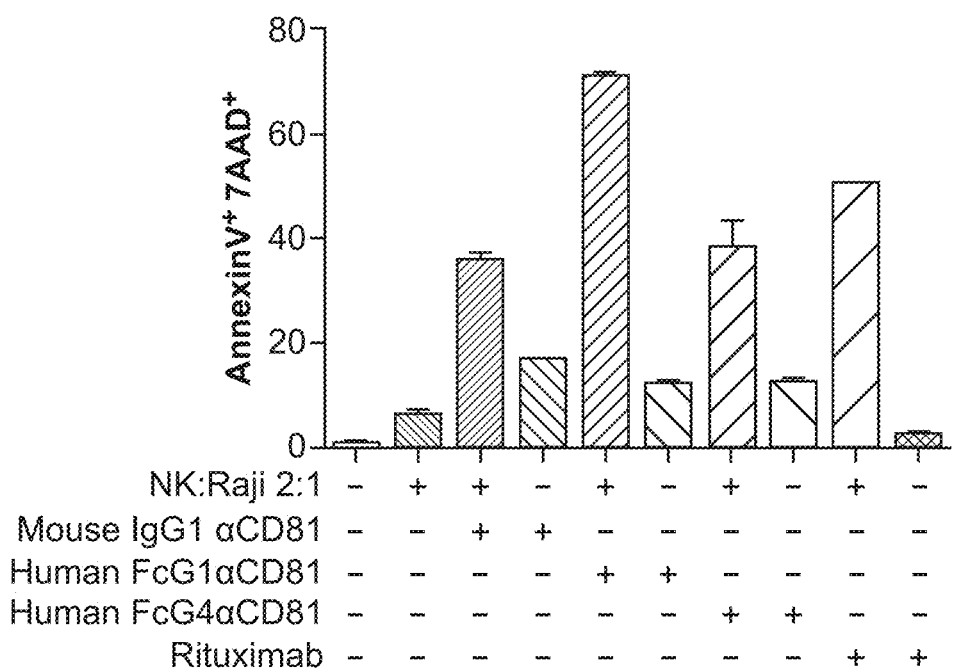

In the context of human effector cells (purified human NK cells), switching the constant region to a human Fc sequence improves ADCC, shown in FIG. 5B. Chimeric anti-human CD81 mAb (SEQ ID NO:1/SEQ ID NO:4 with human heavy chain constant region IgG1 and human light chain region Kappa) was more effective than mouse anti-human CD81 mAb (SEQ ID NO:1/SEQ ID NO:4 with mouse constant region IgG1), it is also more effective than Rituximab in NK cell-mediated antibody dependent cell cytotoxicity (ADCC).

In the context of human effector cells (purified human NK cells), humanized anti-human CD81 antibodies better mediated ADCC and direct killing of Raji cells than Rituximab, shown in FIG. 5C. Humanized anti-human CD81 mAbs (H1L1 SEQ ID NO:2/SEQ ID NO:5 with human heavy chain constant region IgG1 and human light chain region Kappa) and H2L1 (SEQ ID NO:3/SEQ ID NO:5 with human heavy chain constant region IgG1 and human light chain region Kappa) were as effective as the chimeric anti-CD81 antibody, and more effective than Rituximab.

The activity of the antibody in mediating complement dependent cytotoxicity was highly augmented by the use of mouse IgG2a constant region, or human IgG1 constant region, shown in FIG. 6A. By contrast, mouse IgG1 and human IgG4 poorly mediated CDC.

As shown in FIG. 6B, complement dependent cytotoxicity mediated by chimerized anti-human CD81 IgG1 (SEQ ID NO:1/SEQ ID NO:4 with human heavy chain constant region IgG1 and human light chain region Kappa) and by humanized anti-human CD81 IgG1 (SEQ ID NO:3/SEQ ID NO:5 with human heavy chain constant region IgG1 and human light chain region Kappa) antibodies was highly superior to that of mouse anti-human CD81 IgG1.

Figure 7A:
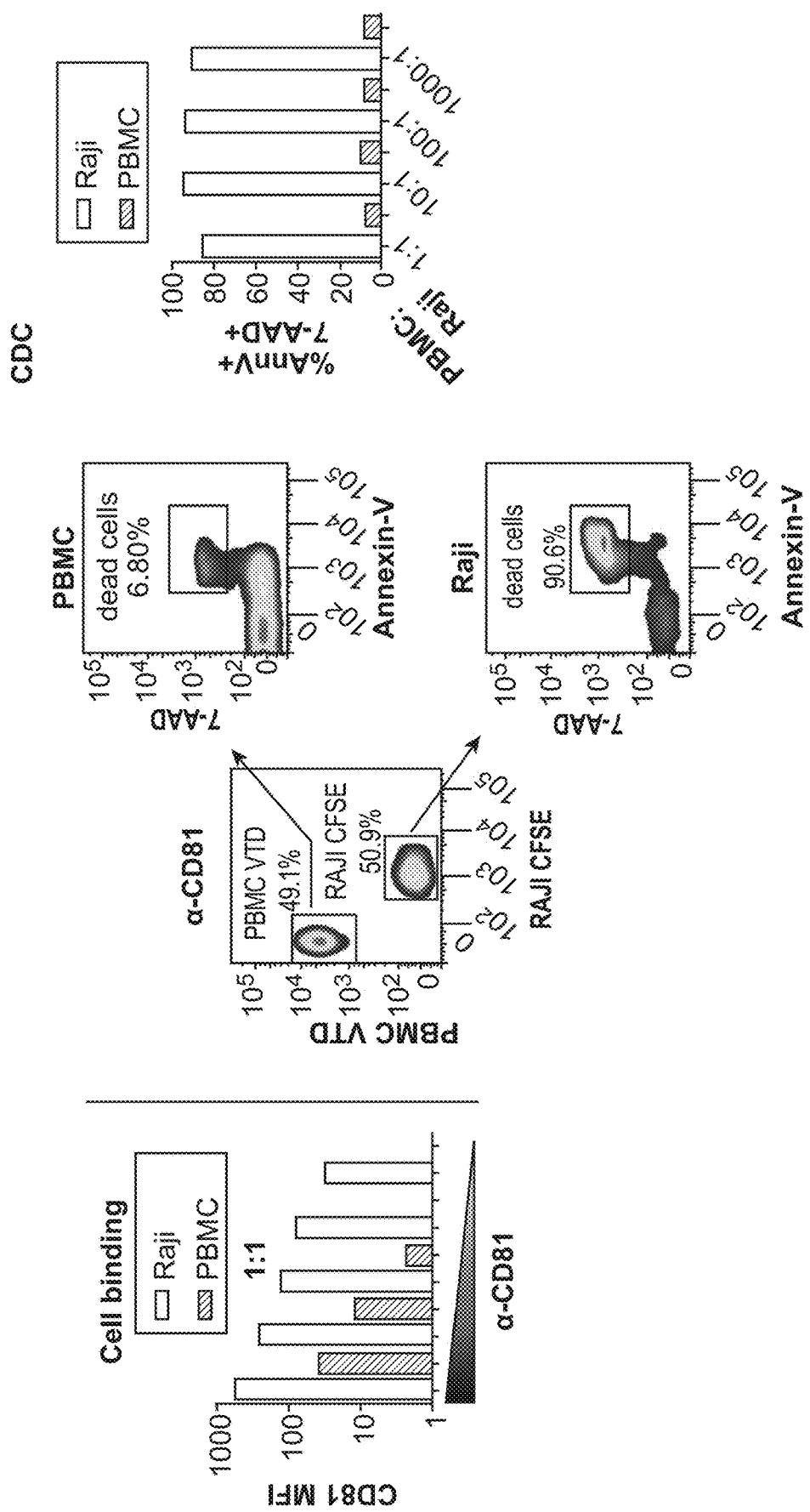
FIG. 7A-7B.
Figure 7B:
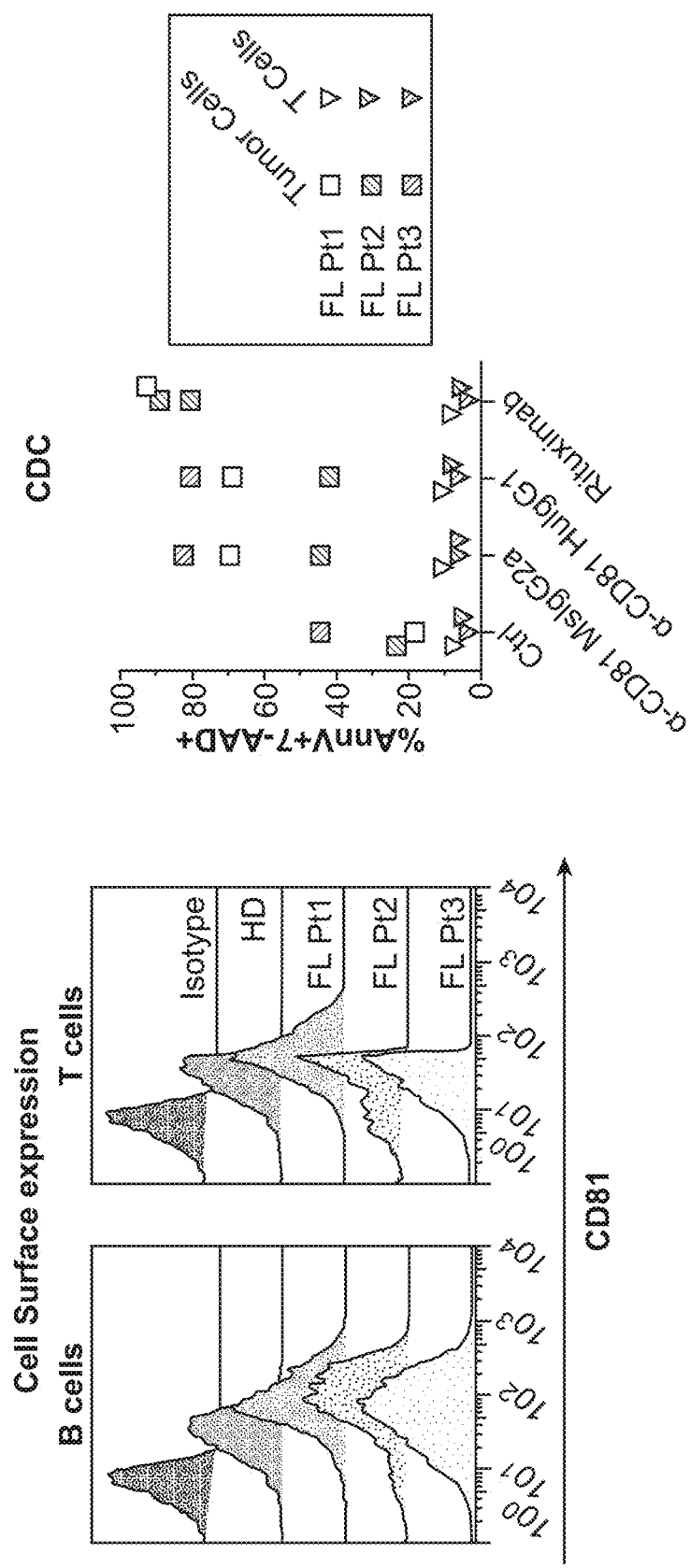

Tumor cells (Raji) cells were more effective than PBMC (derived from a healthy donor) at binding mouse anti-human CD81 antibody 5A6, especially at lower antibody concentrations, and are more sensitive to anti-CD81-mediated CDC even when present at a 1:1000 ratio, shown in FIG. 7A. Patient-derived lymphoma B cells were also more sensitive to CD81-mediated CDC than normal T cells present in the same biopsy specimen, shown in FIG. 7B. CD81 is expressed on follicular lymphoma (FL) tumor B cells, as well as on normal T cells within biopsies of FL samples. CDC mediated killing by mouse anti-human CD81 antibody (SEQ ID NO:1/SEQ ID NO:4 with mouse constant region IgG2a) on tumor B and normal T cells of the same FL patient reveals that tumor B cells are more sensitive than normal T cells to 5A6-mediated killing. The same results were obtained using the chimeric anti-human CD81 antibody (SEQ ID NO:1/SEQ ID NO:4 with human heavy chain constant region IgG1 and human light chain constant region kappa).

What is claimed is:

1. An isolated chimeric or humanized antibody that specifically binds to human CD81, and comprises a variable heavy region with CDR1, CDR2 and CDR3 from SEQ ID NO:1, and a variable light region with CRD1, CDR2 and CDR3 from SEQ ID NO:4.

2. The antibody of claim 1, wherein the heavy chain variable region comprises the amino acid sequence set forth in SEQ ID NO:1, 2 or 3.

3. The antibody of claim 2, wherein the variable heavy region further comprises a human Fc.

4. The antibody of claim 3, wherein the human Fc is an IgG.

5. The antibody of claim 4, wherein the IgG provides for high ADCC activity.

6. The antibody of claim 3, wherein the Fc region engineered for enhanced ADCC activity.

7. The antibody of claim 6, wherein the Fc region comprises glyco-engineered carbohydrate side chains.

8. The antibody of claim 6, wherein the Fc region comprises amino acid substitutions that enhance binding to FcγRIIIA.

9. The antibody of claim 1, wherein the light chain variable region comprises the amino acid sequence set forth in SEQ ID NO:4, 5 or 6.

10. The antibody of claim 1, further comprising amino terminal amino acid residues linked by cleavable linkers.

11. A method of reducing breast cancer or lymphoma metastasis in a human subject in need thereof, the method comprising the step of administering to a subject a therapeutically effective amount of an isolated chimeric or humanized antibody that specifically birds to human CD81, and comprises a variable heavy region with CDR1, CDR2 and CDR3 from SEQ ID NO:1, and a variable light region with CDR1, CDR2 and CDR3 from SEQ ID NO;4.

* * * * *

UNITED STATES PATENT AND TRADEMARK OFFICE
CERTIFICATE OF CORRECTION

| | |
|---|---|
| PATENT NO. | : 10,815,306 B2 |
| APPLICATION NO. | : 16/308113 |
| DATED | : October 27, 2020 |
| INVENTOR(S) | : Shoshana Levy et al. |

It is certified that error appears in the above-identified patent and that said Letters Patent is hereby corrected as shown below:

In the Specification

Column 1 Line 11 Insert "STATEMENT OF GOVERNMENT SUPPORT":
--This invention was made with Government support under contract W81XWH-14-1-0397 awarded by the Department of Defense. The Government has certain rights in the invention.--

Signed and Sealed this
Second Day of May, 2023

Katherine Kelly Vidal
*Director of the United States Patent and Trademark Office*